(12) United States Patent
He et al.

(10) Patent No.: US 12,048,684 B2
(45) Date of Patent: Jul. 30, 2024

(54) ARCTIGENIN LIQUID NANO-PREPARATION AND PREPARATION METHOD THEREOF

(71) Applicants: Wuhan Academy of Agricultural Sciences, Wuhan (CN); Hubei Wudang Animal Pharmaceutical Co., Ltd., Chengguan Town (CN)

(72) Inventors: Bin He, Wuhan (CN); Lijun Wu, Wuhan (CN); Zheng Lu, Wuhan (CN); Zhiping Ran, Wuhan (CN); Guoming Chen, Wuhan (CN); Zhiyong Shao, Wuhan (CN); Xiabing Chen, Wuhan (CN); Wei Liu, Wuhan (CN); Ying Li, Wuhan (CN); Wu Liu, Wuhan (CN); Qi Zhou, Wuhan (CN); Wenhai Yang, Wuhan (CN); Dongqing Liu, Wuhan (CN); Kangyu Du, Wuhan (CN)

(73) Assignees: Wuhan Academy of Agricultural Sciences, Wuhan (CN); Hubei Wudang Animal Pharmaceutical Co., Ltd., Chengguan Town (CN)

( * ) Notice: Subject to any disclaimer, the term of this patent is extended or adjusted under 35 U.S.C. 154(b) by 0 days.

(21) Appl. No.: 17/988,031

(22) Filed: Nov. 16, 2022

(65) Prior Publication Data
US 2024/0100015 A1 Mar. 28, 2024

(30) Foreign Application Priority Data
Sep. 22, 2022 (CN) .......................... 202211159865.3

(51) Int. Cl.
| | | |
|---|---|---|
| *A61K 31/365* | (2006.01) |
| *A61K 9/107* | (2006.01) |
| *A61K 9/14* | (2006.01) |
| *A61K 36/23* | (2006.01) |
| *A61K 36/54* | (2006.01) |
| *A61K 47/10* | (2017.01) |
| *A61K 47/44* | (2017.01) |

(52) U.S. Cl.
CPC ............ *A61K 31/365* (2013.01); *A61K 9/107* (2013.01); *A61K 9/14* (2013.01); *A61K 36/23* (2013.01); *A61K 36/54* (2013.01); *A61K 47/10* (2013.01); *A61K 47/44* (2013.01)

(58) Field of Classification Search
CPC ........ A61K 31/365; A61K 9/107; A61K 9/14; A61K 36/23; A61K 36/54; A61K 47/10; A61K 47/44
See application file for complete search history.

(56) References Cited

U.S. PATENT DOCUMENTS

2014/0056830 A1* 2/2014 Pather .................. A61K 8/9789
424/59

FOREIGN PATENT DOCUMENTS

WO WO-2011120339 A1 * 10/2011 ........... A61K 31/365

\* cited by examiner

*Primary Examiner* — Frederick F Krass
*Assistant Examiner* — Lucy M Tien
(74) *Attorney, Agent, or Firm* — Thomas| Horstemeyer, LLP

(57) ABSTRACT

The present disclosure provides an arctigenin liquid nano-preparation and a preparation method thereof, and relates to the technical field of pharmaceutical preparation. In the present disclosure, arctigenin is prepared into a liquid nano-preparation, having advantages of distribution of a droplet diameter on nanoscale, significantly increased specific surface area, rapid absorption, and high bioavailability. Meanwhile, nano-preparation entered the body can be captured by wandering leucocytes, and a medicament is delivered to inflammatory lesions through chemiotaxis, thereby conferring a targeted drug delivery feature on the arctigenin and making a therapy more targeted.

8 Claims, 1 Drawing Sheet

ARCTIGENIN LIQUID NANO-PREPARATION AND PREPARATION METHOD THEREOF

CROSS REFERENCE TO RELATED APPLICATION

This patent application claims the benefit and priority of Chinese Patent Application No. 202211159865.3, filed with the China National Intellectual Property Administration on Sep. 22, 2022, the disclosure of which is incorporated by reference herein in its entirely as part of the present application.

TECHNICAL FIELD

The present disclosure relates to the technical field of pharmaceutical preparation, in particular to an arctigenin liquid nano-preparation and a preparation method thereof.

BACKGROUND

Arctigenin is an active ingredient of burdock, and it is a crystalline powder in appearance. It is indicated that arctigenin has better anti-inflammatory, immunoregulatory, antiviral, and antitumor activity, and has wide application prospect in pharmaceutical industry. However, due to poor water solubility of arctigenin, the arctigenin has a weak targeting ability in vivo after clinical use, leading to low actual bioavailability of the drug. Therefore, the dosage of the arctigenin actually distributed in the inflammatory area is low after the arctigenin enters the body, and the efficacy cannot be fully exerted.

SUMMARY

An objective of the present disclosure is to provide an arctigenin liquid nano-preparation and a preparation method thereof, increasing water solubility and bioavailability of arctigenin.

To achieve the above objective, the present disclosure provides the following technical solution:

The present disclosure provides an arctigenin liquid nano-preparation, including an aqueous phase, an oil phase, an emulsifier, and a co-emulsifier; arctigenin is dissolved in the oil phase; the oil phase is dispersed in the aqueous phase to form an oil-in-water structure; the arctigenin liquid nano-preparation has a droplet diameter of less than 100 nm.

Preferably, the oil phase may include cinnamon oil, coriander oil, and sesame oil.

Preferably, the cinnamon oil, the coriander oil, and the sesame oil in the oil phase may have a mass ratio of (0.5-2.5):(1.0-6.0):(2.0-4.0).

Preferably, the arctigenin liquid nano-preparation may include, on a per 100 g basis, 0.1-3.0 g of the arctigenin, 0.5-2.5 g of the cinnamon oil, 1.0-6.0 g of the coriander oil, 2.0-4.0 g of the sesame oil, 21-35 g of the emulsifier, 2.0-5.0 g of the co-emulsifier, and balance being water.

Preferably, the arctigenin liquid nano-preparation may include, on a per 100 g basis, 0.5-2.5 g of the arctigenin, 1.0-2.0 g of the cinnamon oil, 2.0-5.0 g of the coriander oil, 2.5-3.5 g of the sesame oil, 23-33 g of the emulsifier, 2.5-4.5 g of the co-emulsifier, and the balance being water.

Preferably, the arctigenin liquid nano-preparation may include, on a per 100 g basis, 1.5 g of the arctigenin, 1.5 g of the cinnamon oil, 3.5 g of the coriander oil, 3.0 g of the sesame oil, 28.0 g of the emulsifier, 3.5 g of the co-emulsifier, and the balance being water.

Preferably, the emulsifier may include Tween-20 and PEG-40 hydrogenated castor oil; the Tween-20 and the PEG-40 hydrogenated castor oil may have a mass ratio of (15-25):(6-10).

Preferably, the co-emulsifier may include propane-1,2-diol.

Preferably, the arctigenin liquid nano-preparation may have a droplet diameter of less than 50 nm.

The present disclosure provides a preparation method of the arctigenin liquid nano-preparation according to the above technical solution, including the following steps:

dissolving arctigenin in an oil phase to obtain an arctigenin-dissolved oil phase; and mixing the arctigenin-dissolved oil phase with an emulsifier and a co-emulsifier, and under stirring and sonication, adding water to a resulting mixture system for emulsification to obtain the arctigenin liquid nano-preparation, where the sonication is conducted at a frequency of 40 kHz.

The present disclosure provides an arctigenin liquid nano-preparation, including an aqueous phase, an oil phase, an emulsifier, and a co-emulsifier; the arctigenin is dissolved in the oil phase; the oil phase is dispersed in the aqueous phase to form an oil-in-water structure; the arctigenin liquid nano-preparation has a droplet diameter of less than 100 nm.

In the present disclosure, the arctigenin is prepared into a liquid nano-preparation, having advantages of distribution of a droplet diameter on nanoscale, significantly increased specific surface area, rapid absorption, and high bioavailability. Meanwhile, nano-preparation entered the body can be captured by wandering leucocytes, and a medicament is delivered to inflammatory lesions through chemiotaxis, thereby conferring a targeted drug delivery feature on the arctigenin and making a therapy more targeted.

Moreover, in the present disclosure, the arctigenin is dissolved in an oil phase, and the oil phase is dissolved in water by emulsification to further make the arctigenin dissolve in the water and increase water solubility of the arctigenin. In one aspect, the bioavailability is increased; in another aspect, the arctigenin can be prepared into injections, oral liquids, and other dosage forms, which are more advantageous in administration methods compared with preparing the arctigenin into tablets, capsules, and other solid dosage forms having difficulty in swallowing.

Further, the present disclosure selects the cinnamon oil, the coriander oil, and the sesame oil as carriers of the arctigenin. In one aspect, a mixed oil phase composed of the three oils can ensure that the nano-preparation prepared from the arctigenin has high drug loading and meets the desired stability; in another aspect, the cinnamon oil has the actions of dispelling wind-damp and warming the spleen and stomach, the coriander oil has the actions of invigorating the stomach, dispelling wind, and dispelling phlegm, the sesame oil has the actions of moisturizing dryness, detoxifying, relieving pain, and dispersing swelling, the three oils with these actions, together with the arctigenin, constitute a compound preparation, significantly improving the efficacy of disease treatment.

DETAILED DESCRIPTION OF THE EMBODIMENTS

Figure 1:
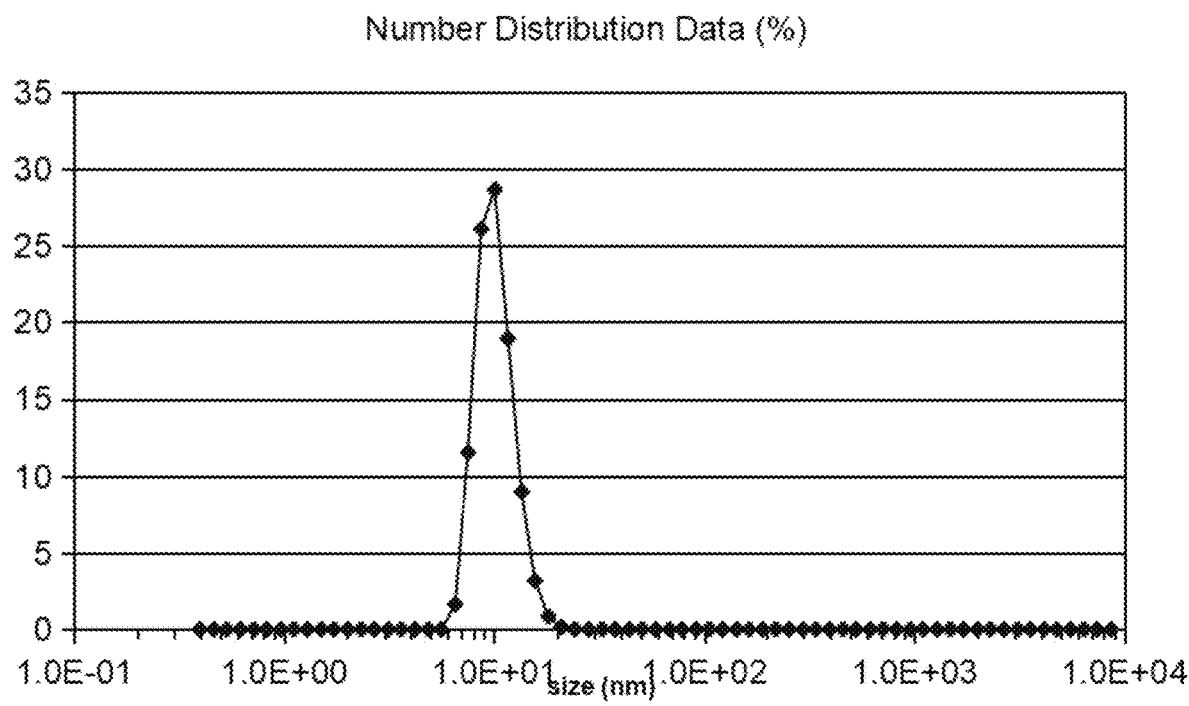
FIG. 1 illustrates particle size distribution of an arctigenin liquid nano-preparation prepared in Example 1.
Figure 2:
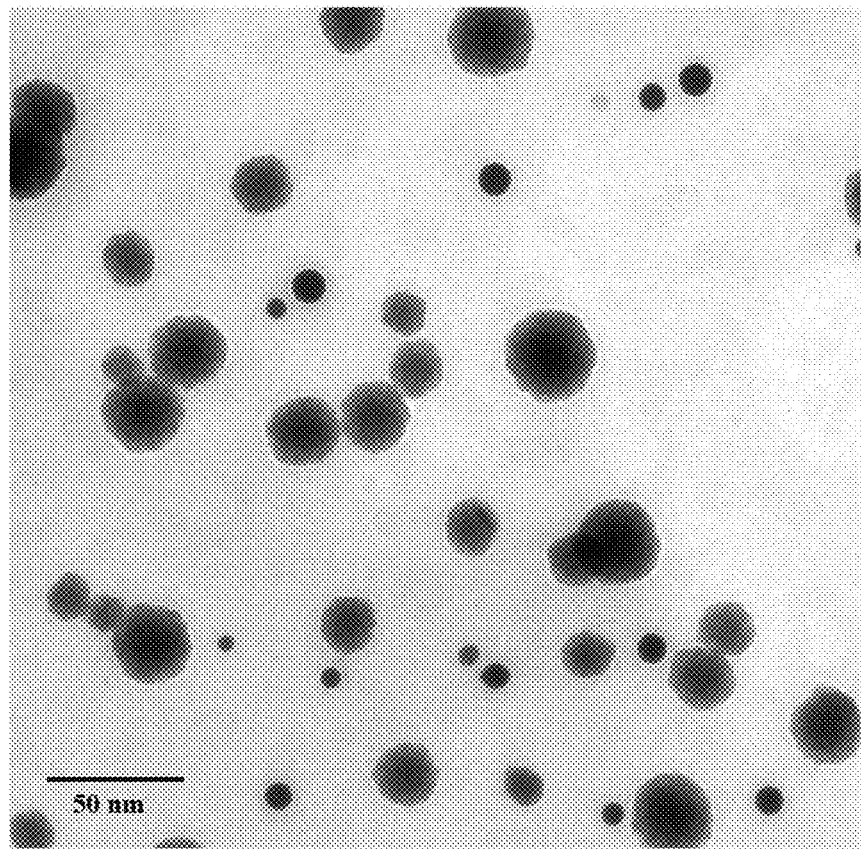
FIG. 2 is a scanning electron microscopy (SEM) image of an arctigenin liquid nano-preparation prepared in Example 1.

The present disclosure provides an arctigenin liquid nano-preparation, including an aqueous phase, an oil phase, an emulsifier, and a co-emulsifier; arctigenin is dissolved in the oil phase: the oil phase is dispersed in the aqueous phase to form an oil-in-water structure; the arctigenin liquid nano-preparation has a droplet diameter of less than 100 nm.

In the present disclosure, the aqueous phase may preferably be deionized water.

In the present disclosure, the oil phase may preferably include cinnamon oil, coriander oil, and sesame oil: the cinnamon oil, the coriander oil, and the sesame oil in the oil phase may preferably have a mass ratio of (0.5-2.5):(1.0-6.0):(2.0-4.0), more preferably (1.0-2.0):(2.0-5.0):(2.5-3.5), and further preferably 1.5:3.5:3.

In the present disclosure, the emulsifier may preferably include Tween-20 and PEG-40 hydrogenated castor oil; the Tween-20 and the PEG-40 hydrogenated castor oil may preferably have a mass ratio of (15-25):(6-10), more preferably (16-24):(7-9), and further preferably 20:8. In the present disclosure, the emulsifier mainly plays a role in emulsifying the oil phase and dissolving both the arctigenin and the oil phase in the aqueous phase, while forming nanoscale droplets.

In the present disclosure, the co-emulsifier may preferably include propane-1,2-diol. The co-emulsifier can enhance the stability of the liquid nano-preparation and prevent emulsion breaking during later storage.

In the present disclosure, the arctigenin liquid nano-preparation provided by the present disclosure, on a per 100 g basis, may preferably include 0.1-3.0 g of the arctigenin, 0.5-2.5 g of the cinnamon oil, 1.0-6.0 g of the coriander oil, 2.0-4.0 g of the sesame oil, 21-35 g of the emulsifier, 2.0-5.0 g of the co-emulsifier, and balance being water; more preferably, the arctigenin liquid nano-preparation may include 0.5-2.5 g of the arctigenin, 1.0-2.0 g of the cinnamon oil, 2.0-5.0 g of the coriander oil, 2.5-3.5 g of the sesame oil, 23-33 g of the emulsifier, 2.5-4.5 g of the co-emulsifier, and the balance being water; further preferably, the arctigenin liquid nano-preparation may include 1.5 g of the arctigenin, 1.5 g of the cinnamon oil, 3.5 g of the coriander oil, 3.0 g of the sesame oil, 28.0 g of the emulsifier, 3.5 g of the co-emulsifier, and the balance being water.

In the present disclosure, the arctigenin liquid nano-preparation may preferably have a droplet diameter of less than 50 nm, more preferably <40 nm, and further preferably 1-35 nm.

The present disclosure provides a preparation method of the arctigenin liquid nano-preparation according to the above technical solution, including the following steps:

- dissolving arctigenin in an oil phase to obtain an arctigenin-dissolved oil phase; and
- mixing the arctigenin-dissolved oil phase with an emulsifier and a co-emulsifier, and under stirring and sonication, adding water to a resulting mixture system for emulsification to obtain the arctigenin liquid nano-preparation, where the sonication is conducted at a frequency of 40 kHz.

In the present disclosure, the arctigenin is dissolved in the oil phase to obtain the arctigenin-dissolved oil phase. In the present disclosure, the oil phase may preferably be obtained by mixing the cinnamon oil, the coriander oil, and the sesame oil. The present disclosure has no particular requirement on the process of the dissolution.

In the present disclosure, after the arctigenin-dissolved oil phase is obtained, the arctigenin-dissolved oil phase is mixed with the emulsifier and the co-emulsifier, and under stirring and sonication, the water is added to the resulting mixture system for emulsification to obtain the arctigenin liquid nano-preparation; the sonication is conducted at a frequency of 40 kHz.

The present disclosure has no particular requirement on a process of mixing the arctigenin-dissolved oil phase with the emulsifier and the co-emulsifier, as long as a uniform mixing method known to the art may be used.

The present disclosure has no particular requirement on stirring rate, as long as stirring rate known to the art may be used. In the present disclosure, the sonication is controlled at a frequency of 40 kHz, ensuring the formation of a particle size at the nanoscale and the stability of an emulsion.

The present disclosure has no particular requirement on the duration of the stirring and the sonication. The stirring and the sonication may be stopped until the system is changed from a liquid state to a pasty semi-solid state, followed by a liquid state; subsequently, the system is cooled down to room temperature to obtain the arctigenin liquid nano-preparation.

The arctigenin liquid nano-preparation and the preparation method thereof provided by the present disclosure will be described in detail below with reference to the examples, but they should not be construed as limiting the protection scope of the present disclosure.

Example 1

1.5 g of cinnamon oil, 3.5 g of coriander oil, and 3.0 g of sesame oil were mixed, 1.5 g of arctigenin was dissolved under stirring, and an arctigenin-dissolved oil phase was obtained.

20.0 g of Tween-20 was mixed well with 8.0 g of PEG-40 hydrogenated castor oil, followed by 3.5 g of propane-1,2-diol; subsequently, the resulting mixture was put in the arctigenin-dissolved oil phase, stirred well and sonicated at 40 kHz; while stirring, 59.0 g of deionized water was added, and the system was changed from a liquid state to a pasty semi-solid state, followed by a liquid state; subsequently, the system was cooled down to room temperature and shaken well again to obtain an arctigenin liquid nano-preparation.

After measurement by a laser granularity analyzer and observation under an electron microscope, the results are shown in FIGS. 1 and 2. The particle size of the arctigenin liquid nano-preparation provided by the present disclosure was distributed between 5 and 28 nm, and its particles were spherical or spheroid in overall morphology.

The arctigenin raw material was added to pure water at room temperature, and its solubility was <0.05%, but the water solubility of the arctigenin in Example 1 of the present disclosure was up to 1.5% (namely 100 g of the arctigenin liquid nano-preparation provided by the present disclosure contained 1.5 g of arctigenin, enabling the dissolution of 1.5 g of arctigenin in the water) and the arctigenin was able to be diluted in the water infinitely. After the water solubility was increased, regardless of absorption into the blood or the tissue fluid, the bioavailability would be increased significantly because either the blood or the tissue fluid is a system mainly composed of water.

Example 2

0.5 g of cinnamon oil, 1.0 g of coriander oil, and 2.0 g of sesame oil were mixed, 0.1 g of arctigenin was dissolved under stirring, and an arctigenin-dissolved oil phase was obtained.

15.0 g of Tween-20 was mixed well with 6.0 g of PEG-40 hydrogenated castor oil, followed by 2.0 g of propane-1,2-diol; subsequently, the resulting mixture was put in the arctigenin-dissolved oil phase, stirred well and sonicated at 40 kHz; while stirring, 73.4 g of deionized water was added, and the system was changed from a liquid state to a pasty semi-solid state, followed by a liquid state; subsequently, the system was cooled down to room temperature and shaken well again to obtain an arctigenin liquid nano-preparation. After measurement by a laser granularity analyzer, the particle size distribution was shown between 3 and 30 nm.

Example 3

2.5 g of cinnamon oil, 6.0 g of coriander oil, and 4.0 g of sesame oil were mixed, 3.0 g of arctigenin was dissolved under stirring, and an arctigenin-dissolved oil phase was obtained.

25.0 g of Tween-20 was mixed well with 10.0 g of PEG-40 hydrogenated castor oil, followed by 5.0 g of propane-1,2-diol; subsequently, the resulting mixture was put in the arctigenin-dissolved oil phase, stirred well and sonicated at 40 kHz; while stirring, 44.5 g of deionized water was added, and the system was changed from a liquid state to a pasty semi-solid state, followed by a liquid state; subsequently, the system was cooled down to room temperature and shaken well again to obtain an arctigenin liquid nano-preparation. After measurement by a laser granularity analyzer, the particle size distribution was shown between 3 and 30 nm.

The foregoing descriptions are merely preferred implementations of the present disclosure. It should be noted that several improvements and modifications can be made by a person of ordinary skill in the art without departing from the principles of the present disclosure, and these improvements and modifications should be deemed as falling within the protection scope of the present disclosure.

What is claimed is:

1. An arctigenin liquid nano-preparation, comprising an aqueous phase, an oil phase, an emulsifier, and a co-emulsifier, wherein arctigenin is dissolved in the oil phase, the oil phase is dispersed in the aqueous phase to form an oil-in-water structure, and the arctigenin liquid nano-preparation has a droplet diameter of less than 100 nm wherein the oil phase comprises cinnamon oil, coriander oil, and sesame oil, and the cinnamon oil, the coriander oil, and the sesame oil in the oil phase have a mass ratio of (0.5-2.5):(1.0-6.0):(2.0-4.0); and the emulsifier comprises polyethylene glycol sorbitan monolaurate and PEG-40 hydrogenated castor oil; and the polyethylene glycol sorbitan monolaurate and the PEG-40 hydrogenated castor oil have a mass ratio of (15-25):(6-10);

wherein on a per 100 g basis, the arctigenin liquid nano-preparation comprises 0.1-3.0 g of the arctigenin, 0.5-2.5 g of the cinnamon oil, 1.0-6.0 g of the coriander oil, 2.0-4.0 g of the sesame oil, 21-35 g of the emulsifier, 2.0-5.0 g of the co-emulsifier, and balance being water.

2. The arctigenin liquid nano-preparation according to claim 1, comprising, on a per 100 g basis, 0.5-2.5 g of the arctigenin, 1.0-2.0 g of the cinnamon oil, 2.0-5.0 g of the coriander oil, 2.5-3.5 g of the sesame oil, 23-33 g of the emulsifier, 2.5-4.5 g of the co-emulsifier, and the balance being water.

3. The arctigenin liquid nano-preparation according to claim 2, comprising, on a per 100 g basis, 1.5 g of the arctigenin, 1.5 g of the cinnamon oil, 3.5 g of the coriander oil, 3.0 g of the sesame oil, 28.0 g of the emulsifier, 3.5 g of the co-emulsifier, and the balance being water.

4. The arctigenin liquid nano-preparation according to claim 1, wherein the co-emulsifier comprises propane-1,2-diol.

5. The arctigenin liquid nano-preparation according to claim 2, wherein the co-emulsifier comprises propane-1,2-diol.

6. The arctigenin liquid nano-preparation according to claim 3, wherein the co-emulsifier comprises propane-1,2-diol.

7. The arctigenin liquid nano-preparation according to claim 1, wherein the arctigenin liquid nano-preparation has a droplet diameter of less than 50 nm.

8. A preparation method of the arctigenin liquid nano-preparation according to claim 1, comprising the following steps:

dissolving the arctigenin in the oil phase to obtain an arctigenin-dissolved oil phase; and mixing the arctigenin-dissolved oil phase with the emulsifier and the co-emulsifier, and under stirring and sonication, adding water to a resulting mixture system for emulsification to obtain the arctigenin liquid nano-preparation, wherein the sonication is conducted at a frequency of 40 KHz.

\* \* \* \* \*